United States Patent
Spears

[19]

[11] Patent Number: 6,080,105
[45] Date of Patent: Jun. 27, 2000

[54] ILLUMINATED DENTAL AND SURGICAL RETRACTOR AND KIT INCLUDING PLURALITY OF BLADES AND BLADES RECHARGING BASE

[76] Inventor: Robert A. Spears, P.O. Box 3768, Sparks, Nev. 89432

[21] Appl. No.: 08/882,913

[22] Filed: Jun. 26, 1997

[51] Int. Cl.[7] .................................................. A61B 17/00
[52] U.S. Cl. ...................... 600/212; 600/213; 600/237; 600/245; 600/246
[58] Field of Search .................. 600/191, 192, 600/193, 199, 201, 210, 212, 123, 237, 240, 241, 242, 245, 246; 433/31, 30, 140, 93

[56] References Cited

U.S. PATENT DOCUMENTS

| | | | |
|---|---|---|---|
| 990,277 | 4/1911 | Lauderdale | 600/242 X |
| 2,161,151 | 6/1939 | Freedman | 32/33 |
| 2,186,143 | 1/1940 | Neugass | 600/245 X |
| 2,296,793 | 9/1942 | Kirschbaum | 128/20 |
| 2,840,070 | 6/1958 | Tofflemire | 128/11 |
| 2,885,537 | 5/1959 | Wood, Jr. | 600/241 X |
| 3,349,764 | 10/1967 | Edinger et al. | 600/241 X |
| 4,337,763 | 7/1982 | Petrassevich | 128/20 |
| 4,344,419 | 8/1982 | Burgin | 600/246 X |
| 4,643,172 | 2/1987 | Taff et al. | 600/241 X |
| 5,036,835 | 8/1991 | Filli | 600/199 X |
| 5,152,686 | 10/1992 | Duggan et al. | 433/93 |
| 5,271,734 | 12/1993 | Takeuchi | 433/72 |
| 5,355,870 | 10/1994 | Lacy | 600/241 |
| 5,457,611 | 10/1995 | Verderber | 362/32 |

*Primary Examiner*—Jeffrey A. Smith
*Attorney, Agent, or Firm*—David S. Thompson

[57] ABSTRACT

An illuminated retractor provides a handle and a blade, the blade having a forward portion composed of a light transmissive material. The forward portion blade of the extends from handle and is formed suitably for retraction of body tissue adjacent to a body cavity to be illuminated. The handle is manually grippable and houses an electrical power source which powers a lamp mounted in blade. The forward portion of the blade is formed of a light transmissive material in optical communication with the lamp and is formed for the emission of an unfocused and diffused light for general illumination of the cavity. A surface region of the blade body may be frosted or ground so as to widely diffuse light emitted from lamp, thereby illuminating a wide area of a body cavity. A plurality of interchangeable blades of diverse shapes includes a perio-ostial elevator tip and a dental cheek retractor. A blank blade is provided which can easily be customized into a variety of shapes. In another embodiment, the blade has at least one mirrored reflecting surface in combination with frosted diffused light emitting surfaces.

18 Claims, 7 Drawing Sheets

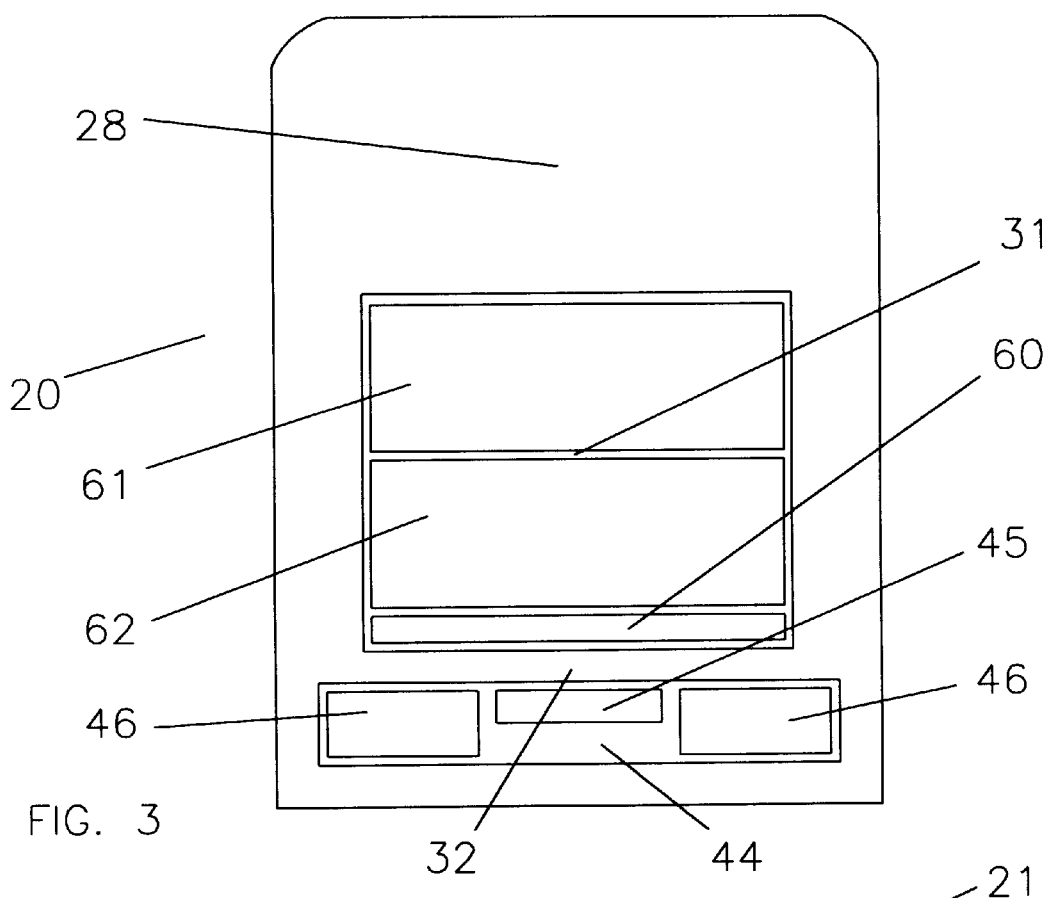
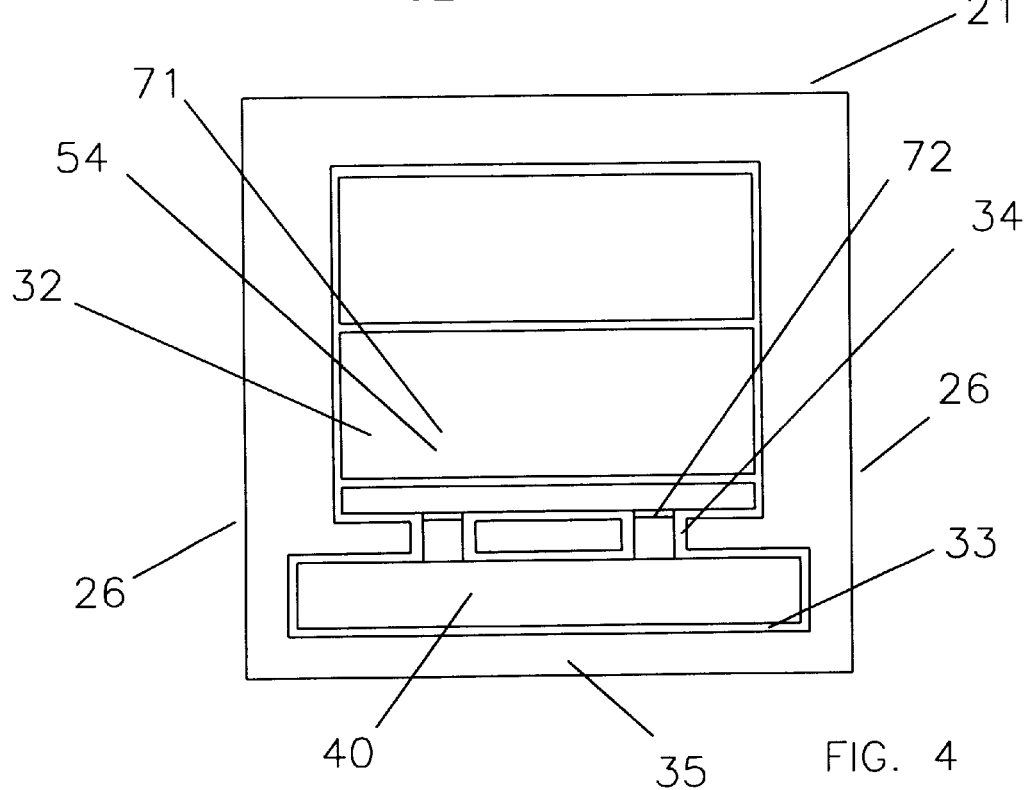

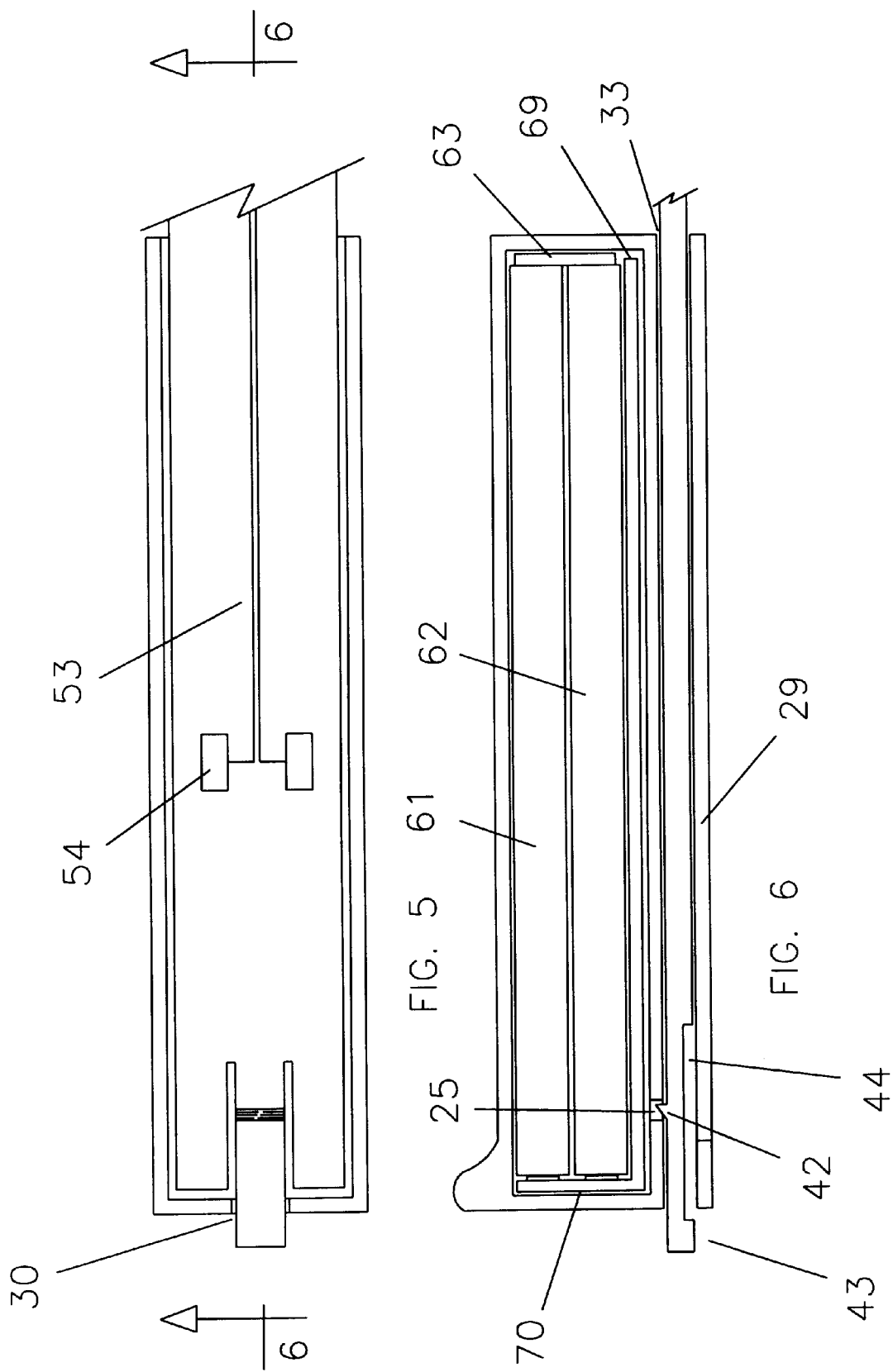

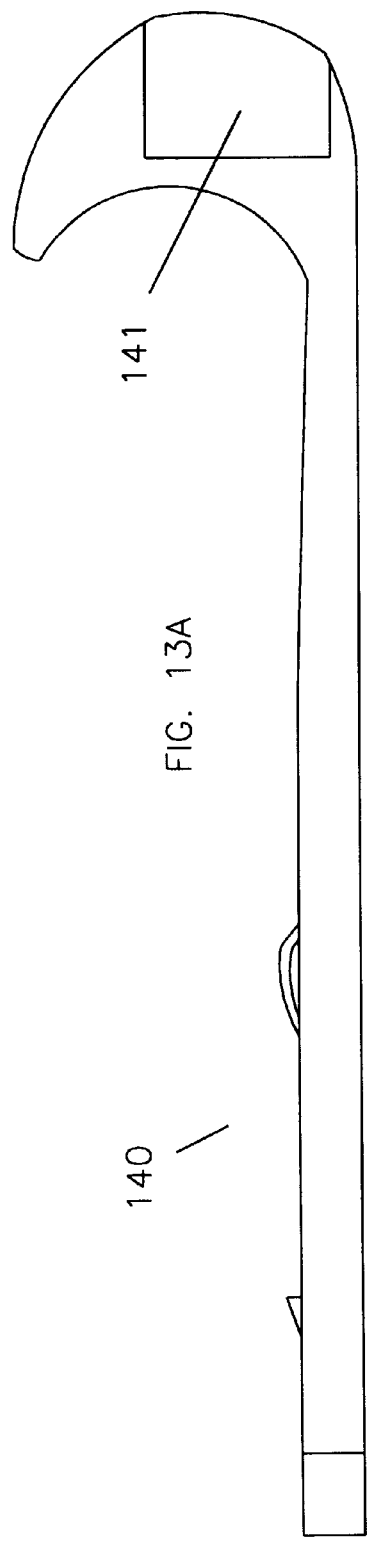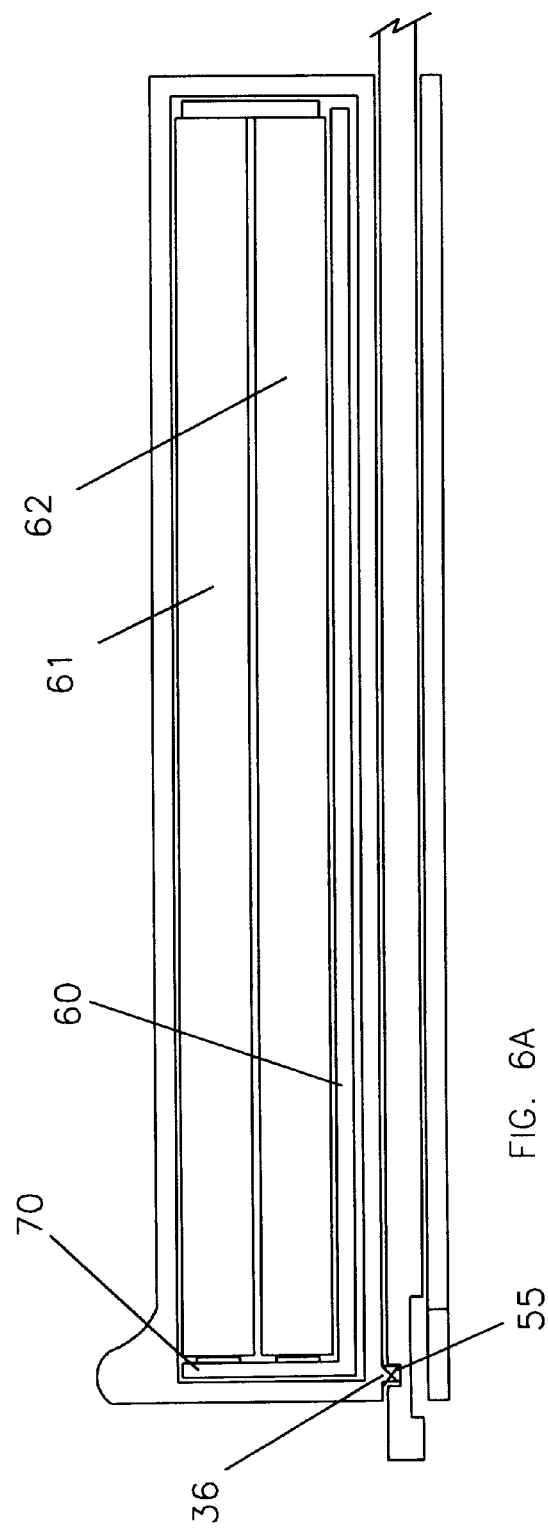

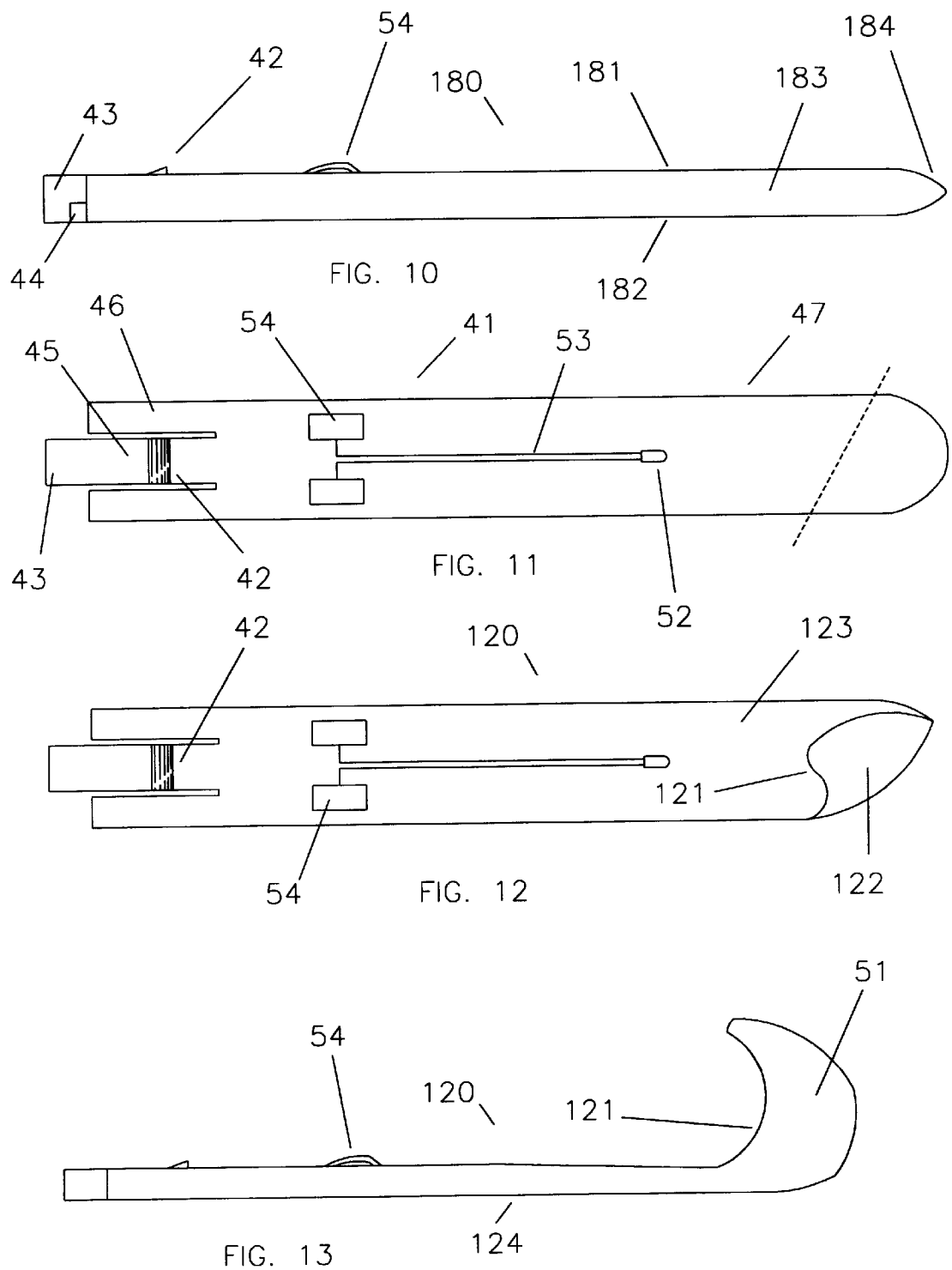

ILLUMINATED DENTAL AND SURGICAL RETRACTOR AND KIT INCLUDING PLURALITY OF BLADES AND BLADES RECHARGING BASE

CROSS-REFERENCES

There are no applications related to this application filed in this or any foreign country.

BACKGROUND

Dental and surgical retractors, elevators which are push/pull instruments are used to manipulate various regions of the patient's skin, flesh or tissue. Using such an instrument, flesh or tissue may be folded or held away from a location where a dental or surgical operation or other intervention is being performed. In the dental industry retractors, elevators and other instruments are used most commonly to push or pull the patient's cheeks, tongue and soft tissues from the site where the operator is working. Retractors which pull away and elevators which push away these portions of flesh realize the following objectives: The body cavity wherein the operation is being performed is increased in size, thus allowing for more room in which to perform the procedure, concomitantly it allows for more room to maneuver the operating and diagnostic tools. Additionally, by pulling this flesh away from the operating work site, better visibility is achieved as more light is able to enter the cavity where the operator is working. Another function is to separate tissue from the underlying architecture and soft tissue related to the surgical site, giving access to previously covered areas.

Surgical instruments are typically comprised of two permanently fastened parts, the first part being a body or handle portion and the second part being a blade portion. This body or handle portion is held by the operator when using the retractor. The blade can be curved to lift portions of the skin or soft tissues, or hook around the tongue. By inserting a hook-shaped blade into an open cavity, and then rotating it, the surrounding tissues or the tongue thereby grasped can be retracted and pulled out of the working environment.

A single retractor blade size and shape design is usually too limited to perform all possible retracting functions. It has instead proven much better to use a plurality of differently shaped and sized retractors, elevators which are adapted to handle different types and masses of body tissues. The variety of sizes and shapes that can be used to perform retracting and reflecting functions are very numerous. These can range from large hook shaped instruments, to small perio-ostial elevator shapes that separate tissue from the underlying foundation. This variety of needs has required dentists, surgeons and others in the medical field to use different retractors, elevators and assorted instruments during different procedures.

Sufficient illumination of the mouth and other body cavities is also required to properly conduct dental, surgical and many other procedures. Accordingly, these instruments are typically used in conjunction with lighting systems wherein the retractor holds the body tissue out of the way while a lighting system concurrently illuminates the body cavity produced. Often in dental situations, relying on directed lighting external to the mouth can provide problems due to difficulties projecting the light in the required direction and thus create shadows which are cast onto the operating field. The use of separate retracting and lighting systems can cause inconvenience for the operator who is forced to simultaneously manipulate both systems. Various problems may occur when these separate lighting and retracting tools get in the way of each other and also of other equipment at the working environment. As a result, some systems have sought to integrate both of these functions into a single illuminated operating device. Unfortunately, these systems have all tended to emit narrow spot beam of light which is directed at a rather small location at the operating site. As the retractor is moved, as is necessary to perform its very retracting function, the narrow spot beam of light produced by these illuminated retractors is concurrently moved around the cavity in various directions. Consequently, the competing needs to properly position both the illumination function and the retractor function have tended to limit the effectiveness of these illuminated operating systems.

A system exists for use in the dental industry as a saliva ejector which may carry a source of light illuminating a patient's mouth when the instrument is in use. U.S. Pat. No. 2,161,151 to Hyman is an example of such a system. As the primary function of this system is to remove saliva from the patient's mouth, the ejector must be positioned to receive the pooling of saliva in the lower portion of the mouth . Accordingly, the Hyman system could not be used as a general purpose retractor in he surgical or dental fields, as the Hyman system is not at all designed to act as a movable retractor as it must remain relatively stationary and directed downwards in the patient's mouth.

A dental appliance exists for tongue stabilizing and debris removal from the mouth during the performance of dental procedures, as is found in U.S. Pat. No. 5,152,686 to Duggan, et al. This apparatus includes a bite block mad of a formable material and is uniquely formed to mold with the shape of the mouth cavity in the region of the tongue. This specialized device is not designed to be used as a general purpose dental or surgical retractor, nor is it adapted to be used at any location on the body, other than the mouth.

A system exists for holding and directing the beam of high intensity light sources, such as halogen or krypton gas-filled lamps, during dental or surgical procedures. An example of such a system is found in U.S. Pat. No 5,457,611 to Verderber. This system is not adapted to act as any sort of retractor, but simply direct a narrow spot beam towards a particular location.

A dental device exists for emitting light beams to measure the depth of gum pockets. An example of such a system is found in U.S. Pat. No. 5,271,734 to Takeuchi. This device uses a plurality of light emitting notches or grooves near the probe tip, these notches being spaced to form a rule. This device is not adapted to be used as a dental or surgical retractor.

A variety of illuminated surgical retractors exist which can be used to illuminate the interior of a natural body cavity or a cavity formed by an incision or wound. An example of such a system is found in U.S. Pat. No. 4,337,763 to Petrassevich. The device provides illumination from a light bulb location found somewhat to the rear of the blade. Altering the position of the retractor correspondingly alters the position towards which the light beam is directed. This system does not provide a plurality of interchangeable blades of different sizes and shapes. In addition, this illuminated retractor does not provide a diffused light, but rather the light is directed from a fixed point source.

Another example of a light directing surgical retractor instrument is found in U.S. Pat. No. 2,840,070 to Tofflemier. This device mounts a lamp at the rear face of a parabolic-shaped reflector which operates to focus and direct the light to where it is needed. This device has a curved portion which operates as a retractor, while the lamp and parabolic mirror are positioned on the inside of the tissue to be retracted. This device does not provide a diffuse light, but rather provides a concentrated directed beam. In addition, this device is limited in the particular uses to which it can be put, due to its unusual non S-shape, its large bulky nature, and the fact that a large parabolic mirror is attached to its end. In contrast, typical dental or surgical retractors typically end in a much sharper point end which is used for probing and separating the body's tissue A final example of an illuminated surgical retractor is found in U.S. Pat. No. 2,296,793 to Kirschbaum. This device consists of a body portion and a blade with a lamp embedded in the blade. The blade is hollow with the bulb being located at a point where direct rays pass down to the end of the blade and out through a small transparent closure at the end of the blade. The Kirschbaum system has several limitations. First, the light emitted from the retractor is emitted only through a small opening at the end of the retractor's blade. This design presents two problems. First, the Kirschbaum system does not provide a gentle, even and diffused light illuminating the entire cavity into which it is placed. Rather, only a narrow directed spot beam passes out of the end of the blade. As this retractor is moved, the light beam will correspondingly be moved in direction. Secondly, as the light beam is emitted only from the retractor at the end of its tip, this will tend to block the beam when the retractor is in use, as the end of the retractor will be placed against or dug down into the body tissue which is to be pulled by the retractor. Accordingly, the light source will tend to become obscured when the lighted end tip of the blade becomes immersed in blood or tissue.

Consequently, the need exists for an illuminated instrument that provides a gentle diffused light rather than a narrow directed spot beam to the body cavity, thus operating as a diffused light which will more evenly illuminate a much wider area of the dark cavity in which the operation is being performed than can be done with previous narrow directed beam systems. The objective is to supply a well dispersed and relatively even illumination to the work area while performing the function of the dental/surgical retractor. The blades do a specific chore, they are designed to be the desired instrument needed for a specific modality. The unique frosting of the bladed instrument creates a very even source of light not blinding to the user. The emitted light is very diffuse in nature penetrating the deeper tissues, creating the ability to see in and through the tissues in the operating environment. The light emitted by this instrument is well dispersed and relatively even in intensity which is not hard on the eyes of the operator. This illuminated device will also perform all the functions of a dental, surgical retractor or elevator. This device has a blade shaped specifically for hooking around and pulling back, dragging or lifting and/or pushing or pulling body tissues. The light source is found within the body of the blade of the instrument, it is not located so close to the tip of the blade that the light source will tend to become obscured when a lighted tip of the blade becomes immersed in body and tissue fluids.

Furthermore, an assortment of differently sized and shaped illuminated blades will also be provided to perform the various required functions presently performed by a set of conventionally sized and shaped instruments. These illuminated blades will preferably also be freely interchangeable with the handle of the body portion of this instrument. It is also preferable when providing this plurality of differently shaped blades, to provide a blank blade made up of the same material as other blades which can be quickly and easily formed, at the job site, to shape and thereby be a customized blade for use in the device. Lastly, it is also preferable to have this illuminated system cordless so that it can be easily held and manipulated by an operator, free from the problems of the cumbersome cords that could possibly tangle with other equipment.

In view of the limitations of the prior art, there is a need for illuminated dental and surgical retractor that provides a handle that is adapted to carry any of a plurality of differently designed blades, wherein each blade provides an internally mounted bulb capable of providing a diffused illuminating light.

SUMMARY

The present invention is directed to an apparatus that satisfies the above needs. A novel illuminated dental and surgical retractor provides some or all of the following structures.

(A) A manually grippable handle defining a blade insertion channel and a battery compartment within the handle.

(B) A circuit card, carried within the battery compartment. The circuit card provides a body running the length of the handle and a perpendicular end portion adjacent to the back of the handle. The circuit card body carries electrical contacts engaged by the blade or by a recharger station.

(C) Any of a number of blades are releasably attachable to the handle. The typical blade provides:

(a) A rear portion, defining left and right side bars and a center bar defining a lower cavity. The rear portion is insertable into the manually grippable handle.

(b) A fastening tang, and corresponding tang recess, allow the blade to attach to the handle in a releasable manner.

(c) Electrical contacts, carried by an upper surface of the rear portion of the blade, engage electrical contacts carried by the body of the circuit card, upon blade insertion.

(d) A forward portion of the blade, extending from the handle, is usable by a dentist or surgeon in manipulating and illuminating tissue. In the preferred embodiment of the invention, the forward portion of the blade is constructed of transparent material, although translucent material may also be used. In the preferred embodiment of the invention, the forward portion of the blade provides frosted or mirrored surface areas, although optically clear surfaces could also be used.

(e) A lamp is enclosed within the forward portion of the blade, and is electrically connected to the batteries by the circuit card and spring contacts.

It is an object of the present invention to provide an illuminated retractor or instrument for use in dentistry, surgery or for use in diagnosis in paramedical fields.

It is a further object of the present invention to provide an illuminated retractor having a handle portion and interchangeable curved blades.

It is a further object of the present invention to provide an illuminated retractor which emits a gentle, diffused and even light which is not directed in any one particular direction, rather than emitting a narrower directed or focused beam.

It is a further object of the present invention to provide an illuminated retractor which produces a gentle diffused and even light such that the dentist or surgeon using the retractor may view any area of the illuminated body cavity. It is a further object that this diffused light provides constant panoramic illumination regardless of the positioning or movement of the retractor.

It is a further object of the present invention to provide an illuminated retractor having a blade with a body which is formed of a light transmissive transparent or translucent material, and with a lamp mounted inside this blade. It is a further object that this transparent or translucent blade material be formed for the emission of a diffused light therethrough from all portions of the blade engaging the tissue for unfocused general illumination of the cavity. This light transmissive blade can be made with a frosted or ground surface which is not fully transparent and thereby diffuses the light emitted from a lamp inside the blade of the device. If the surface of the blade body is ground to achieve this frosted appearance, it is a further object of this grinding to customize the shape of the blade.

It is a further object of the present invention to provide an illuminated retractor having a lamp embedded in its blade and powered by a power source in its body portion.

It is a further object of the present invention to provide an illuminated retractor having automatically turned on when the blade is attached to the body portion of the retractor.

It is a further object of the present invention to provide an illuminated retractor which is cordless and operates on rechargeable batteries.

It is a further object of the present invention to provide an illuminated retractor having a plurality of differently sized and shaped blades which are freely interchangeable with the body or handle portion of the retractor.

It is a further object of the present invention to provide an illuminated retractor with a plurality of disposable blades.

It is a further object of the present invention to provide an illuminated retractor having a blade which can be individually customized in size and shape through an easy method using readily available common tools.

It is a further object of the present invention to provide an illuminated retractor having a blade which provides illumination and is mirrored on one or more sides.

And a still further object of the present invention to provide an illuminated retractor having a blade which is autoclavable and/or sterilizable.

DRAWINGS

These and other features, aspects, and advantages of the present invention will become better understood with regard to the following description, appended claims, and accompanying drawings where:

FIG. 3 is a cross-sectional view along the 3—3 lines of FIG. 1;

FIG. 4 is a cross-sectional view along the 4—4 lines of FIG. 1;

FIG. 5 is a top cross-sectional view along the 5—5 lines of FIG. 1;

FIG. 6 is a side lengthwise cross-sectional view along the 6—6 lines of FIG. 5;

FIG. 6A is a cross-section similar to FIG. 6, showing an alternate version of the invention having a fastening tang carried by the handle;

FIG. 10 is a side view of a flat blade, having a rounded front edge;

FIG. 11 is a top view of the flat blade of FIG. 10, having a dotted line showing the location of an optional bend that may be made, turning the blade into a dental tongue retractor blade;

FIG. 12 is a top view of a dental tongue retractor blade;

FIG. 13 is a side view of the dental tongue or cheek retractor blade of FIG. 12;

FIG. 13A is side view of the dental tongue or cheek retractor blade of FIG. 13, having the addition of a mirrored surface;

DESCRIPTION

Figure 1:
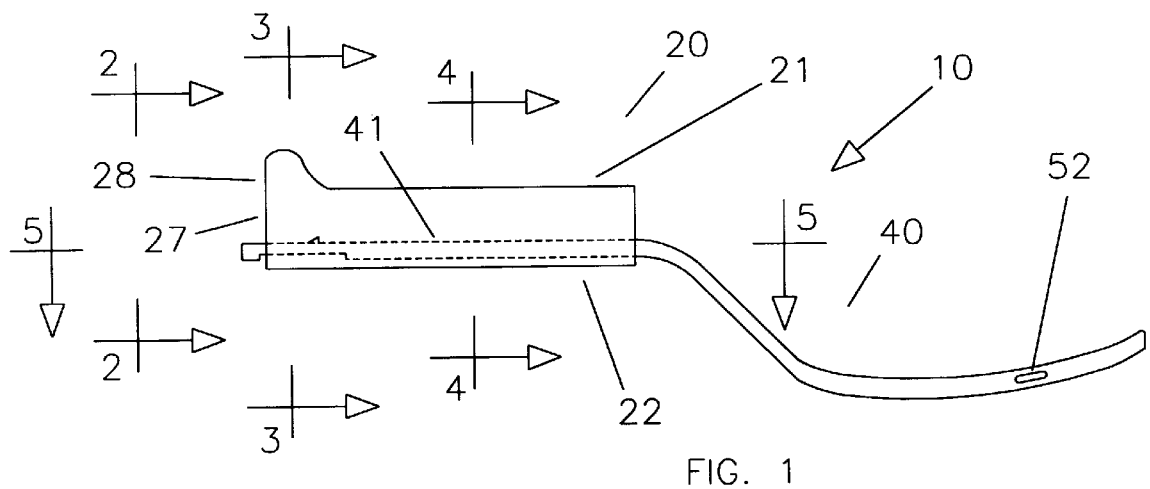
FIG. 1 is a side view of a version of the illuminated dental and surgical retractor of the invention having a gently S-shaped blade installed.

Referring in particular to FIG. 1, an illuminated dental and surgical retractor 10 constructed in accordance with the principles of the invention is seen. The illuminated dental retractor of FIG. 1 provides a handle 20 which encloses a circuit card 60 supporting two batteries. A perio-ostial blade 40, selected from an assortment of blades is releasably held by the handle. Upon insertion of the blade, electrical contacts on the blade communicate with electrical contacts on the circuit card, turning on a lamp 52 carried within the blade.

Figure 2:
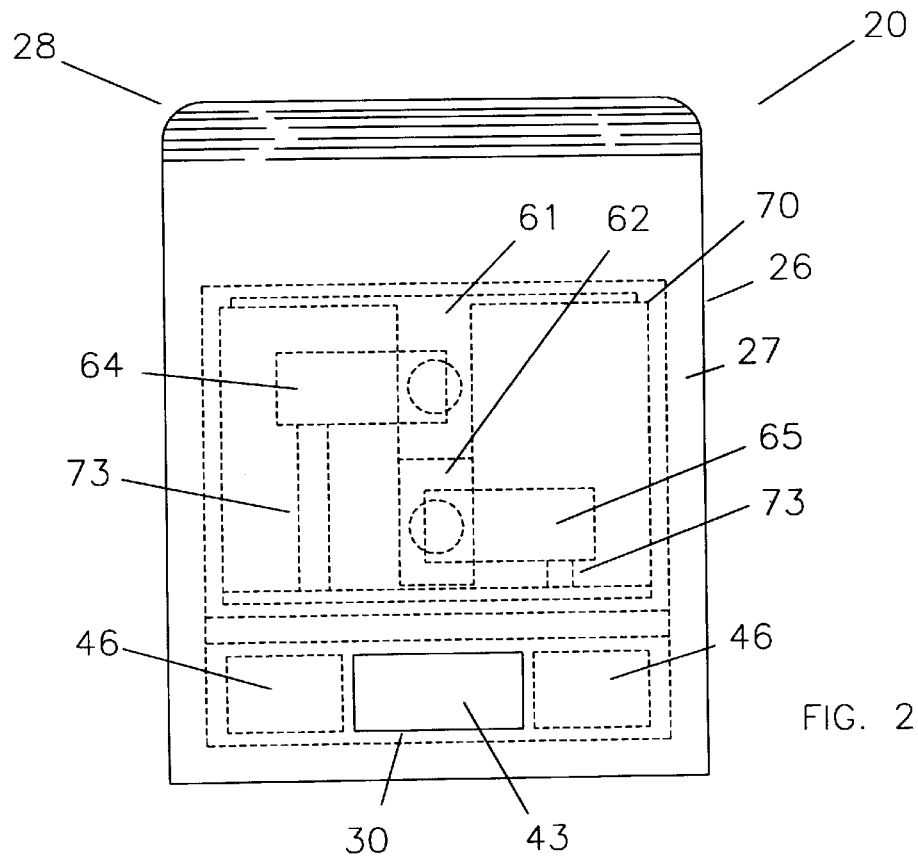
FIG. 2 is an enlarged rear view of the retractor of FIG. 1, showing in dotted outline the rear portion of the circuit card and battery.

Referring in particular to FIGS. 2–6, the details of a preferred version of the handle 20 may be understood. The handle provides top, bottom and side surfaces 21, 22 and 26. The top surface may optionally define a knurled area which provides a better grip for the user, and may optionally provide an indentation the user's thumb. A tail 28, best seen in FIGS. 1–3, prevents the user's hand from sliding rearwardly, thereby enabling the user to pull gently, even where the handle is wet and slippery. The tail may also be used in the same manner as the blade, to retract tissue, although without the illuminating feature of the blade. A back surface 27, best seen in FIG. 2, defines a hole 30 for the center bar 45 and latch release 43 to exit, as seen in FIGS. 1 and 2.

The surfaces of the handle define an interior battery compartment 31, bounded by the top 21, sides 26 and battery compartment floor 32 (FIGS. 3 and 4). In a preferred version of the invention, the battery compartment is hermetically sealed, although this is not necessary for practice of the invention. Two holes 34 in the battery compartment floor 32, best seen in FIG. 4, allow the spring contacts 54 on any blade usable with the handle 20 to come into electrical contact with the electrical connector 71, 72 of the circuit card 60. An area of the upper portion of the battery compartment floor 32 about the holes 34 may be sealed hermetically to a lower portion of the body 69 of the circuit card 60, if desired, by means of glue, caulk or similar substance. In this manner the hermetic seal of the battery chamber may be maintained.

The handle also defines a blade insertion channel 33, which is best seen in FIGS. 3, 4, and 6. The blade insertion channel is bounded by the sides 26, the battery compartment floor 32, and rails 29 or a solid base 35. The blade insertion channel is incrementally larger in cross-sectional area than the blade, and allows for a snug fit.

Referring to FIG. 4, a first version of the invention provides a solid base 35 below the blade 40. In this version of the invention, the solid base 35, sides 26 and the lower surface of the battery compartment floor 32 define a blade insertion channel 33. This arrangement provides a very secure grip of the blade 40.

Figure 4A:
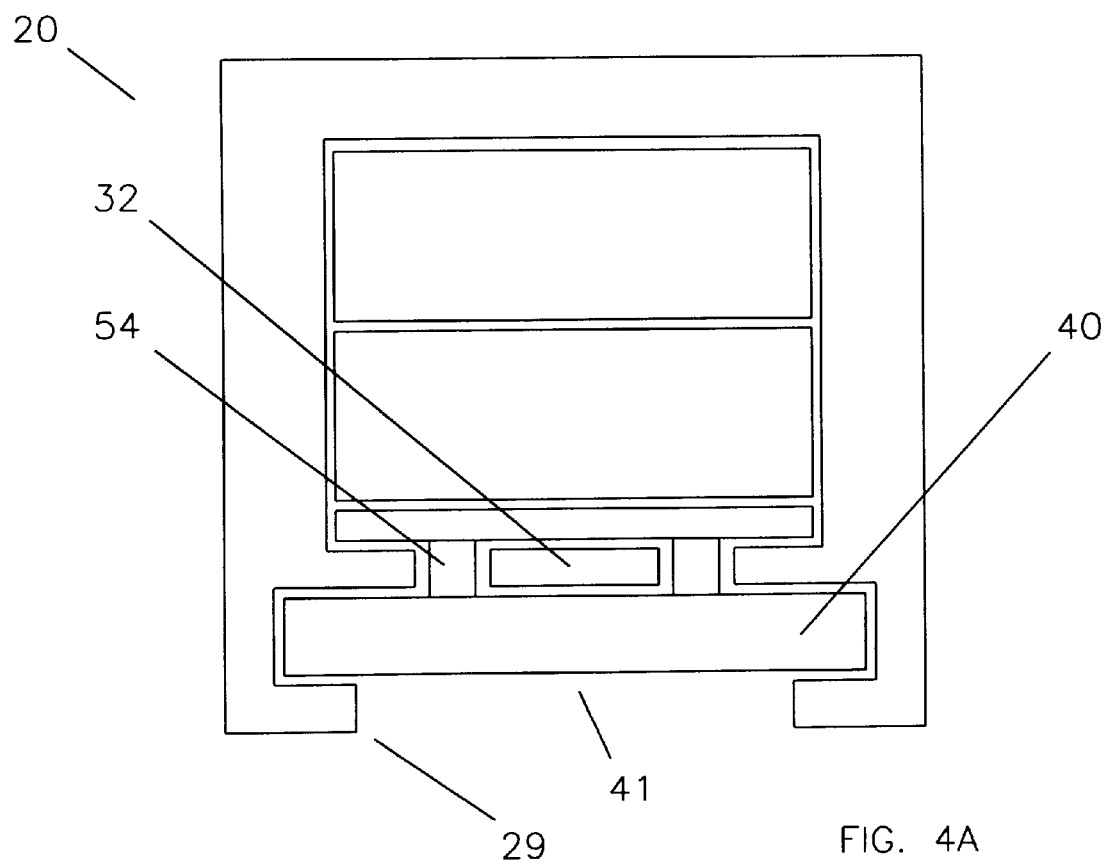
FIG. 4A is a cross-section similar to FIG. 4, showing an alternate version of the invention having lower rails (29) rather than a solid base.

Referring to FIG. 4A, a second version of the invention provides left and right rails 29 to support the bottom of the blade. This arrangement allows easier cleaning of the interior surface of the handle, due to the accessibility of the blade insertion channel 33.

Referring to FIG. 6A, a second version of the means to fasten the blade and handle is disclosed. A tang 36 carried by the handle engages a tang recess 55 on the blade. The tang may be released by depressing the latch release 43.

In a preferred version of the invention, the handle is made of plastic, such as polymethylpentene. However, other materials could be used in a manner consistent with the invention.

A circuit card 60 is best seen in FIG. 2–4 and 6. In a preferred version of the invention, the circuit card carries an upper battery 61 and a lower battery 62, but in other embodiments of the invention a single battery could be employed. Where upper and lower batteries are used, a battery to battery connector 63 is used to link the positive terminal of a first battery to the negative terminal of the second battery.

The circuit card is generally L-shaped when viewed from the side, as in FIG. 6, providing an elongate body 69 and a shorter end section 70. The body carries left and right electrical connectors 71, 72 (FIG. 4) which communicate electrically with the contacts 54 of the blades, as will be further discussed. As seen in FIG. 2, the end piece 70 carries rectangular upper and lower traces attached to battery tabs 64, 65. The tabs 64, 65 pass current to and from the batteries during use of the retractor 10. A conductor 73 connects each battery tab 64, 65 to the blade electrical connector 71, 72 carried by the body 69 of the circuit card for connection to the blade.

The construction of the circuit card may be made of any suitable material, such as plastic or mylar. The circuit card is typically flexible and very thin, and in a preferred version is less than 1/32" thick.

The illuminated dental and surgical retractor 10 of the invention is usable with a variety of blades 40, and the blades disclosed herein are intended to illustrate but not limit the invention. While much diversity is possible in the blades usable with the invention, some elements are shared by all blades in the preferred embodiment of the invention.

A rear portion 41 of the blade 40 inserts into, and is attachable to, the handle 20. A forward portion 40 of the blade extends forwardly, from the handle, as seen in FIG. 1. The rear portion 41 of the blade typically defines a center bar 45 flanked by left and right side bars 46.

The center bar defines a lower cavity 44 and a rearward latch release 43. The lower cavity provides two essential functions. First, upon insertion of the blade into the handle, the cavity 44 allows the blade to deform somewhat, thereby allowing a latching tang 42 carried on the upper surface of the blade to pass through the blade insertion channel 33. Second, the cavity 44 allows the latch release 43 to be operated more easily, in a manner that is best understood by examination of FIG. 6.

The latching tang 42, carried on an upper surface of the center bar 45 of the blade 40, engages a tang recess 25 in the lower surface of the battery compartment floor 32 when the blade is fully inserted into the handle. To release the tang, the latch release portion 43 of the center bar is depressed, releasing the tang 42 from the tang recess 25.

As is best seen in FIGS. 7–13, contacts 54 on the rear portion 41 of the blade make electrical contact with the electrical connectors 71, 72 carried by the circuit card when the blade is inserted into the handle. The contacts of the preferred embodiment are constructed of thin, resiliently deformable, spring metal. As a result, when the blade is inserted into the blade insertion channel 33, the contacts 54 are pressed against the blade. However, when the blade insertion is complete, the contacts resume their erect appearance within the cavities 34 in the battery compartment floor, as seen in FIG. 4. The contacts 54 are connected by wires 53 or other means of electrical connection to a lamp 52. In the preferred embodiment, the lamp 52 is molded into the blade; alternatively the lamp may be installed through a bored hole. In most embodiments of the invention, the lamp is located in a middle area of the forward portion 47 of the blade. Such a location allows for light to diffuse somewhat as it moves through the blade.

In a preferred version of the invention, the area of the blade adjacent to the lamp 52 is typically formed of a generally transparent material 49. A translucent material may alternatively be used.

To soften and diffuse the light emitted from the blade, a ground or frosted finish 51 is applied to the surface of the blade in the preferred embodiment. Such a finish may be made by application of sandpaper or other abrasive material to the blade, or by other known means. Alternatively, where greater light transmission is desired, a non-frosted finish 50 may be used. However, this tends to result in a more focused light, and therefore does not result in desirable diffused lighting.

Figure 8:
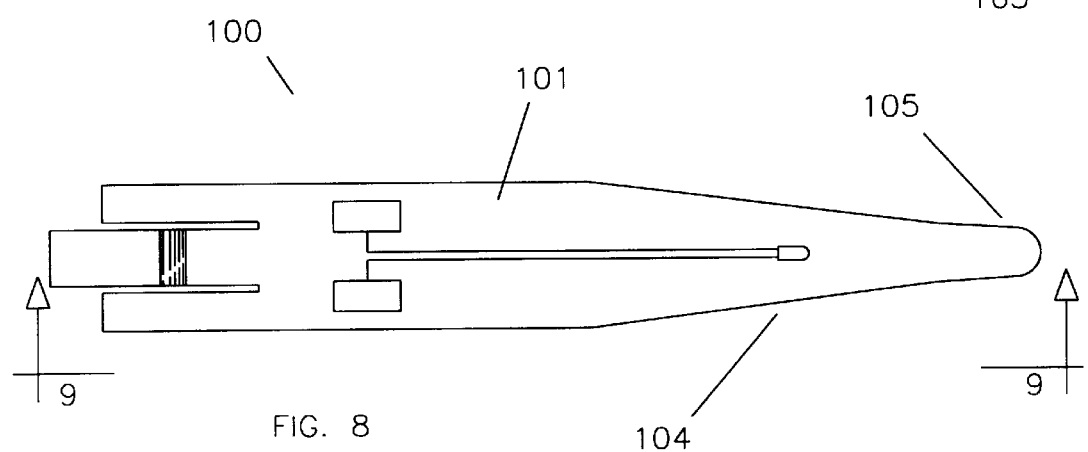
FIG. 8 is a top view of a perio-ostial elevator blade.
Figure 9:
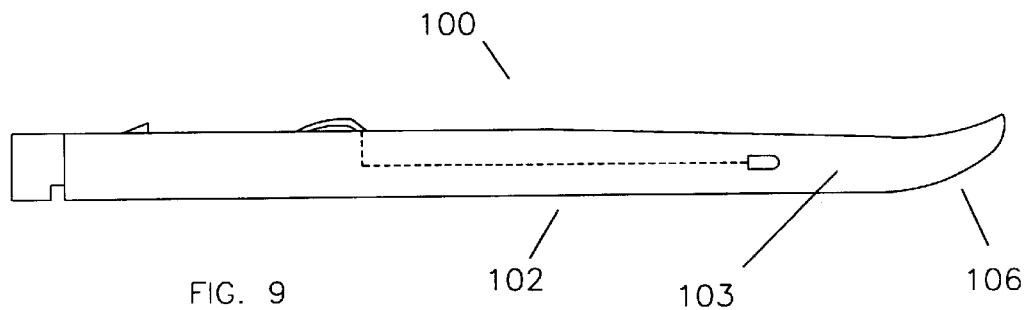
FIG. 9 is a side view of the blade of FIG. 8.

Referring to FIGS. 1, 8 and 9, a perio-ostial elevator blade 100 is seen. Such a blade typically has a gently S-shape, as seen in FIG. 1. Opposed upper surface and lower surfaces 101, 102 are separated by rounded side surfaces 103. Sloping sides 104 converge at a tip 1 05 having a slight curve 106.

A dental tongue retractor blade 120 provides top and bottom surfaces 123, 124 forming inner and outer curved surfaces 121, 122 at the end of the blade. The dental tongue retractor blade is seen in top view in FIG. 12 and in side view in FIG. 13.

Referring to FIG. 13A, a modified dental tongue or cheek retractor blade 140 provides a mirrored finish 141 on the outer curved surface 122. Where such a mirrored surface 141 is provided, the light from the lamp 52 would be emitted from adjacent areas of frosted and non-frosted surface. The mirrored surface could be made from known types of flexible mylar plastic having an adhesive backing.

Optionally, a small area of the tongue retractor blade 140 could be made with a flat surface, over which the mirrored surface could be applied. This would provide better optics.

A flat blade 180 is simple in design, providing opposed top and bottom surfaces 181, 182 joined by side surfaces 183, which may be rounded or square. A rounded end 184 is provided in the example of FIGS. 10 and 11.

Figure 7:
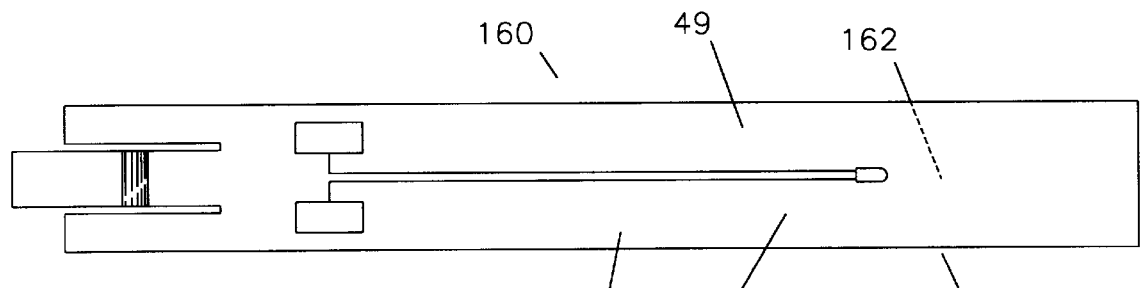
FIG. 7 is a top view of a blank blade.

A further example of a blade usable with the invention is the blank blade 160, seen in FIG. 7. The blank blade in its initial form provides rectilinear top 161, bottom 162 and side 1 63 surfaces, as well as the lamp 52, wiring 53 and electrical contacts seen in the previous blades. The blank blade may be sanded, cut, whittled, bent or twisted, to form almost any desired shape. The blank blade may be made out of either transparent or translucent material, or a mixture of both. A mirrored finish may also be applied to any part of the surface of the blade, as desired.

Figures 14, 15:
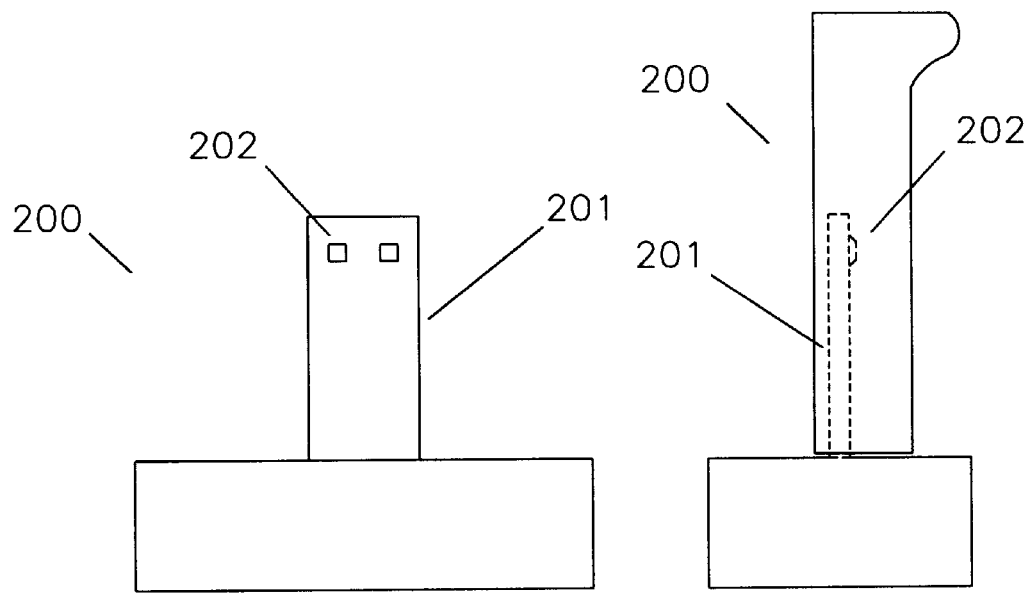
FIG. 14 is a view of the recharging base.
FIG. 15 is a view of the handle in the recharging base.

Referring to FIGS. 14 and 15, a recharging base 200 provides a recharging blade 201 having recharging contacts 202. The recharging blade 201 is sized similar to the rear portion 41 of the blades 40, but is somewhat shorter in length. The recharging contacts 202 are also similar to the contacts 54 on the removable blades 40. The recharging base provides an output of direct current to the contacts 202 by known means, such as a transformer, current rectifier circuit and associated electronics.

A kit of parts usable to practice the invention would include: the handle 20, as described above; at least one blade chosen from among any of those described or suggested by the above description, such as blade 40, perio-ostial elevator blade 100, dental tongue retractor blade 120, dental tongue retractor blade with mirror 140, blank blade 160 or flat blade 180; and the recharging base 200.

To use the illuminated retractor of the invention, the user first selects the blade appropriate for the use from a kit of blades. The rear portion of the blade selected is inserted into the handle 20 until the tang 42 carried by the blade 40 comes into contact with the tang recess 25 of the handle, thereby fastening the blade to the handle. In an alternative version of the invention, the tang 36 carried by the handle would contact a tang recess 55 carried by the blade.

The insertion of the blade into the handle brings blade contacts 54 into electrical communication with the electrical contacts 71, 72 carried by the circuit card 60. Current therefore begins to flow from the batteries 61, 62 through the lamp 52 carried by the blade.

To remove the blade from the handle, the user depresses the latch release 43 of the center bar 45, thereby releasing the tang 42 from the tang recess 25 in a first version of the invention, or the tang 36 from the tang recess 55 in a second version of the invention. Removal of the blade turns the lamp 52 off.

To recharge the batteries 61, 62 attached to the circuit card 60 in the handle 20, the recharging blade 201 of the recharger base 200 is inserted into the blade insertion channel of the handle. This causes the recharger contacts 202 come into contact with the electrical connectors 71, 72 of the circuit card, thereby applying voltage from the recharger base to the batteries.

Although the present invention has been described in considerable detail and with reference to certain preferred versions, other versions are possible. For example, while a limited number of preferred blades have been disclosed in the drawings and text, it is to be understood that a wide variety of other blades could be substitute for use with the handle 20 disclosed. Therefore, the spirit and scope of the appended claims should not be limited to the description of the preferred versions disclosed.

In compliance with the U.S. Patent Laws, the invention has been described in language more or less specific as to methodical features. The invention is not, however, limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. An illuminated retractor comprising:
   (A) a manually grippable handle defining a blade insertion channel;
   (B) a blade releasably attached to the handle, the blade sized for insertion into the blade insertion channel, the blade comprising:
      (a) a forward portion formed of a light transmissive material formed for the emission of a diffused light for unfocused general illumination;
      (b) electrical contacts carried by a surface of the blade; and
      (c) latching means for attachment to the manually grippable handle;
   (C) an electrical power source carried within the handle; and
   (D) an electrically powered light emitting device in optical communication with the forward portion of the blade and mounted within the forward portion of the blade and electrically connected to the power source through the electrical contacts carried by the surface of the blade.

2. The illuminated retractor of claim 1 wherein the forward portion of the blade is formed with opposed side surfaces, each of the side surfaces being suitable for retracting tissue adjacent to a body cavity, and the blade is formed for emission of light from all sides.

3. The illuminated retractor of claim 1 wherein substantially an entire length of the blade is formed of a light transmissive material.

4. The illuminated retractor of claim 1 wherein the power source is carried by a circuit card within the handle, the circuit card having electrical connectors adapted for making electrical contact with the electrical contacts carried by the blade.

5. The illuminated retractor as set out in claim 1 wherein the blade is made of a transparent material.

6. The illuminated retractor as set out in claim 1 wherein, the blade is made of a translucent material.

7. The illuminated retractor as set out in claim 1 wherein, the blade has a frosted surface.

8. The illuminated retractor as set out in claim 7 wherein the frosted surface is formed by grinding the blade length.

9. The illuminated retractor as set out in claim 1 wherein, the electrical power source is a rechargeable battery.

10. The illuminated retractor as set out in claim 1, wherein the light emitting device is turned on by mounting the blade to the handle.

11. The illuminated retractor as set out in claim 1, wherein the lamp is held in an interior bore of the blade.

12. The illuminated retractor as set out in claim 1 wherein, the lamp is cast directly into the material of the blade.

13. The illuminated retractor as set out in claim 1, wherein the blade is formed of a material suitable for custom shaping.

14. The illuminated retractor as set out in claim 1, wherein the blade provides a center bar having a latch release and fastening means for attachment to the handle.

15. The illuminated retractor as set out in claim 14, wherein the blade additionally comprises left and right side bars adjacent to the center bar.

16. The illuminated retractor as set out in claim 1, wherein the blade has at least one mirrored reflecting surface.

17. A kit of parts for illuminating a body cavity of a person, the kit of parts comprising:
   (A) a handle, enclosing a battery;
   (B) a plurality of blades, releasably attachable to the handle, each blade having a lamp carried in a forward portion; and
   (C) a recharging base, having a recharging blade, releasably attachable to the handle.

18. An illuminated dental and surgical retractor, comprising:
 (A) a manually grippable handle defining a blade insertion channel, a tang recess and a battery compartment;
 (B) a battery carried within the battery compartment;
 (C) a first pair of electrical contacts, enclosed by the handle, in electrical communication with the battery; and
 (D) a blade sized for insertion into the blade insertion channel, whereby the blade may be, releasably attached to the handle, the blade comprising:
  (a) a rear portion, defining left and right side bars and a center bar, the center bar defining a lower cavity, the rear portion insertable into the manually grippable handle;
  (b) fastening means, carried by the rear portion, for releasable attachment to the manually grippable handle, comprising a fastening tang;
  (c) a forward portion extending from the handle;
  (d) a lamp, enclosed within the forward portion of the blade; and
  (e) a second pair of electrical contacts, in electrical communication with the lamp, carried by the blade, adjacent to the first pair of electrical contacts when the blade is attached to the handle, whereby upon insertion of the blade into the handle the lamp turns on.

* * * * *